United States Patent [19]

Woo et al.

[11] Patent Number: 5,231,191

[45] Date of Patent: Jul. 27, 1993

[54] RHODAMINE PHOSPHORAMIDITE COMPOUNDS

[75] Inventors: Sam L. Woo, Redwood City; Steven M. Menchen, Fremont; Steven Fung, Palo Alto, all of Calif.

[73] Assignee: Applied Biosystems, Inc., Foster City, Calif.

[21] Appl. No.: 601,961

[22] Filed: Oct. 22, 1990

Related U.S. Application Data

[62] Division of Ser. No. 138,287, Dec. 24, 1987, Pat. No. 4,965,349.

[51] Int. Cl.⁵ .................................................. C07F 9/00
[52] U.S. Cl. .................................... 549/220; 549/223; 549/227; 536/24.3
[58] Field of Search ................. 536/27, 28; 546/15, 546/47, 36, 48, 94, 89, 66; 549/223, 227, 220

[56] References Cited

U.S. PATENT DOCUMENTS

| | | |
|---|---|---|
| 2,153,059 | 4/1939 | Eckert et al. ........................ 546/15 |
| 2,242,572 | 5/1941 | Eckert et al. ........................ 549/227 |
| 3,822,270 | 7/1974 | Reynolds ............................. 546/47 |
| 4,005,092 | 1/1977 | Reynolds ............................. 546/47 |
| 4,965,349 | 10/1990 | Woo et al. .......................... 536/27 |

Primary Examiner—John W. Rollins
Assistant Examiner—J. Oliver Wilson
Attorney, Agent, or Firm—Stephen C. Macevicz; Joseph H. Smith

[57] ABSTRACT

The invention provides a novel cleavage reagent for hydrolysing base-labile linking groups between a solid phase support and oligonucleotides. The cleavage reagent comprises a lower alkyl alcohol, water, and a non-nuccleophilic hindered alkylamine containing from 3 to 6 carbon atoms in a ratio of about 1:1:1 to about 1:3:1, respectively. An important property of the cleavage reagent is that it preserves the fluorescent characteristics of rhodamine dyes during cleavage, thereby making it possible to completely synthesize rhodamine-labeled oligonucleotides by solid phase methods. Rhodamine phosphoramidites are provided to further enhance the efficiency of synthesizing rhodamine-labeled oligonucleotides by such methods.

5 Claims, No Drawings

RHODAMINE PHOSPHORAMIDITE COMPOUNDS

This is a continuation of application Ser. No. 07/138,287, filed Dec. 24, 1987, now U.S. Pat. No. 4,965,349.

FIELD OF THE INVENTION

The invention relates generally to methods of synthesizing oligonucleotides on solid phase supports, and more particularly to methods of labeling synthetic oligonucleotides with fluorescent dyes.

BACKGROUND

Synthetic oligonucleotides find widespread application in molecular biology as probes for screening complementary deoxyribonucleic acid (cDNA) and genomic DNA libraries, and as primers for DNA synthesis by DNA polymerases and reverse transcriptases. The latter applications include techniques for identifying rare messenger RNAs (mRNAs) when partial protein sequence information and a sensitive biological assay for the protein product are available, e.g. as with gamma-interferon, Gray et al., *Nature*, Vol.295, pgs 503–508 (1982), and techniques for sequencing DNA by the dideoxy chain termination method, e.g. Smith et al., *Nucleic Acids Research*, Vol. 13, pgs. 2399–2412 (1985); Schreier et al., *J. Mol. Biol.*, Vol. 129, pgs. 169–172 (1979); and Sanger et al., *J. Mol. Biol.*, Vol. 143, pgs. 161–178 (1980).

Recently, improvements in DNA sequencing methodologies have made use of multiple fluorescent labels to carry out sequencing automatically on a single columnar gel, e.g. Smith et al. (cited above), and Smith et al., *Nature*, Vol. 321, pgs. 674–679 (1986). Typically, the fluorescent labels are attached to the oligonucleotide primers used in such methods in the final step (or series of steps) in the process of constructing primers. Currently, in the phosphitetriester method, prior to removal of the freshly synthesized oligonucleotide from its support up to three additional steps are required to attach a fluorescent label: First, a linking agent is attached to the 5' end of the oligonucleotide under the same conditions used to add nucleoside phosphoramidites. Second, the linking agent is activated, e.g. by removing a protection group to expose a reactive functionality, such as a primary amine. And finally, an activated dye is reacted with the exposed functionality on the linking agent.

Additional complications can arise if one attempts to label the attached oligonucleotide with a rhodamine dye, an important class of dyes in the selection of spectrally resolvable sets of fluorescent labels, e.g. Smith et al. (cited above); and Loken et al, *Cytometry*, Vol. 5, pgs. 152–159 (1984). The primary reagent for cleaving an oligonucleotide from its support also chemically degrades rhodamine dyes radically altering their fluorescent properties. Thus, whenever rhodamine dyes are used in current solid phase synthesis protocols, they must be attached after the oligonucleotide has been cleaved from the solid phase support, which results in an additional step and greater inconvenience in the overall synthesis.

In view of the foregoing, the availability of dye-phosphoramidite conjugates for direct use in solid phase DNA synthesis would improve the efficiency of labeled primer synthesis by reducing the number of steps required to attach a label. In particular, some systems for DNA sequencing would be more amenable to automation if the manual liquid phase synthesis step required for rhodamine attachment could be obviated by the availability of a cleavage reagent which preserved the chemical integrity and fluorescent properties of rhodamine dyes.

SUMMARY OF THE INVENTION

Broadly the invention is directed to a method for synthesizing oligonucleotides labeled with ammonialabile groups. An important aspect of the invention is the cleavage of base-labile linking groups between a solid phase support and an oligonucleotide without ammonia by a cleavage reagent comprising three components: a lower alkyl alcohol having from 1 to 3 carbon atoms, water, and a non-nucleophilic hindered alkylamine containing from 3 to 6 carbon atoms. Preferably, the three components of the cleavage reagent are present in a ratio of about 1:1:1 to about 1:3:1 (by volume), lower alkyl alcohol:water:nonnucleophilic hindered alkylamine. More specifically, the invention includes a method of synthesizing rhodamine-labeled oligonucleotides on a solid phase support. Preferably, this latter method includes the use of rhodamine phosphoramidites in the synthetic process.

Preferably, the non-nucleophilic hindered alkylamine is selected from the group consisting of isopropylamine, t-butylamine, diethylamine, piperidine, t-amylamine, diisopropylamine, and dipropylamine. Most preferably, the non-nucleophilic hindered alkylamine is t-butylamine.

Preferably, the lower alkyl alcohol is selected from the group consisting of methanol, ethanol, and propanol. Most preferably, the lower alkyl alcohol is methanol.

Preferably, the base-labile linking group is a succinate ester. Most preferably, the succinate ester links the oligonucleotide to the solid phase support by way of the 3' hydroxyl group of the oligonucleotide.

An important aspect of the present invention is the cleavage of base labile linking moieties which couple oligonucleotides to solid phase supports, e.g. succinate esters, and/or the removal of base labile amino protection groups, e.g. benzoyl, at the conclusion of oligonucleotide synthesis. Another important aspect of the invention is that the above reactions are carried out without the degradation of rhodamine, thereby making the complete synthesis of rhodamine-labeled oligonucleotides possible on solid phase supports.

DETAILED DESCRIPTION OF THE INVENTION

The invention provides a method of synthesizing oligonucleotides on a solid phase support, particularly oligonucleotides labeled with a rhodamine dye. An important feature of the method is the use of a cleavage reagent (1) which is capable of hydrolyzing the linking group, usually a succinate ester, between the oligonucleotide and the solid phase support so that the oligonucleotide is freed from the solid phase support, (2) which is capable of hydrolyzing the bond between exocyclic amines of the heterocyclic bases of an oligonucleotide and amino protection groups, usually benzoyl or isobutyryl, and (3) which does not alter the chemical structure of rhodamine dyes attached to the oligonucleotide.

Rhodamine dyes used in the invention may be attached to oligonucleotides by a variety of linking means. For example, several means are available for derivatizing oligonucleotides with one or more functionalities that may later be reacted with a appropriately derivatized rhodamine dye. For example, the oligonucleotide may be amino-derivatized and the appropriate rhodamine derivative may be isothiocyanate, N-hydroxysuccinimide, or the like. References disclosing methods for derivatizing oligonucleotides with amino or thiol functionalities include Connolly et al., *Nucleic Acids Research*, Vol. 13, pgs. 4485–4402 (1985); Connolly, *Nucleic Acids Research*, Vol. 15, pgs. 3131–3139 (1987); Ruth, *DNA* Vol. 3, pg.123 (1984); Haralambidis et al., *Nucleic Acids Research*, Vol. 15, pgs. 4857–4876 (1987); and Smith et al., *Nucleic Acids Research*, Vol. 13, pgs. 2399–2412 (1985). Accordingly, these references are incorporated by reference.

Preferably, rhodamine dyes are attached to oligonucleotides as rhodamine phosphoramidites.

The term "cleavage" in reference to solid phase oligonucleotide synthesis means breaking the bond which attaches an oligonucleotide to a solid phase support. Usually, cleavage involves hydrolysis of a succinate ester bond between the 3' hydroxyl of an attached oligonucleotide and the solid phase support.

The term "deprotection" as used herein means removing protection groups from the exocyclic amines of the heterocyclic bases of a oligonucleotide. Usually, deprotection involves hydrolysis of an amide moiety consisting of an exocyclic amine and an amino protection group, e.g. benzoyl or isobutyryl. In the literature the terms "deprotection" is sometimes used more generally, including the removal of protecting groups from the phosphate diesters prior to cleavage. When such protecting groups are methoxy "deprotection" as used herein does not encompass their removal. In this case, additional treatment with a standard thiophenol-containing reagent is required.

As used herein, the term "oligonucleotide" broadly refers to a single stranded chain of either deoxyribonucleotides or ribonucleotides containing a few nucleotides, e.g. 2–20, to many nucleotides, e.g. 20 to several hundred or more. More particularly, the term refers to a single stranded chain of deoxyribonucleotides, in the size range described above.

By "non-nucleophilic" in reference to the alkylamines used in the invention, it is meant that during deprotection (in the presence of the alkylamine) the hydrolysis of the amide protection group will predominate over the competing nucleophilic substitution reaction involving the alkylamine wherein the entire exocyclic amine-protection group complex acts as a leaving group, thus modifying the nucleoside base.

In reference to rhodamine dyes, the *Colour Index* (Association of Textile Chemists, 2nd. Ed., 1971) numbering scheme is used to identify the carbon atoms of the rhodamine dyes. Carbon atoms in the xanthenelike structure are identified by primed numbers as indicated below, and carbon atoms of the 9'-substituted phenyl are identified by unprimed numbers as indicated below.

Preferably, rhodamine dyes for use with the invention are selected from the group defined by the following formula:

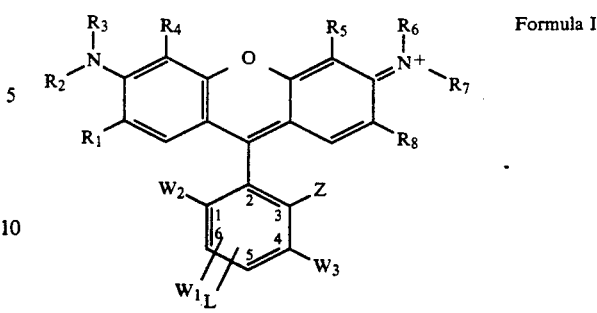

Formula I wherein:

Z is an anionic group, preferably carboxylate or sulfonate, and more preferably carboxylate.

$R_1$ and $R_8$ taken alone are each hydrogen, halogen, alkyl having from 1 to 8 carbon atoms, alkylether having from 1 to 8 carbon atoms, or alkylthioether having from 1 to 8 carbon atoms, and $R_1$ taken together with $R_2$ and $R_8$ taken together with $R_7$ are alkyl chains each having from 2 to 5 carbon atoms connecting the 7' carbon to the nitrogen attached to the 6' carbon and connecting the 2' carbon to the nitrogen attached to the 3' carbon, respectively. Preferably, $R_1$ and $R_8$ taken alone are each hydrogen, alkyl having from 1 to 3 carbon atoms, chloro, or alkylether having from 1 to 3 carbon atoms, and $R_1$ taken together with $R_2$ and $R_8$ taken together with $R_7$ each form an alkyl chain having from 2 to 3 carbon atoms connecting the 7' carbon to the nitrogen attached to the 6' carbon and connecting the 2' carbon to the nitrogen attached to 3' carbon, respectively. Most preferably, $R_1$ and $R_8$ taken alone are each hydrogen, and $R_1$ taken together with $R_2$ and $R_8$ taken together with $R_7$ each form an alkyl chain having 3 carbon atoms connecting the 7' carbon to the nitrogen attached to the 6' carbon and connecting the 2' carbon to the nitrogen attached to the 3' carbon, respectively.

$R_2$ and $R_7$ taken alone are each alkyl having from 1 to 8 carbon atoms, and $R_2$ taken together with $R_1$ and $R_7$ taken together with $R_8$ are each alkyl chains having from 2 to 5 carbon atoms as desribed above. Preferably, $R_2$ and $R_7$ taken alone are each alkyl having from 1 to 3 carbon atoms, and $R_2$ taken together with $R_1$ and $R_7$ taken together with $R_8$ are alkyl chains each having from 2 to 3 carbon atoms connecting the 7' carbon to the nitrogen attached to the 6' carbon and connecting the 2' carbon to the nitrogen attached to 3' carbon, respectively. Most preferably, $R_2$ and $R_7$ taken alone are methyl or ethyl, and $R_2$ taken together with $R_1$ and $R_7$ taken together with $R_8$ are alkyl chains each having 3 carbon atoms connecting the 7' carbon to the nitrogen attached to the 6' carbon and connecting the 2' carbon to the nitrogen attached to the 3' carbon, respectively.

$R_3$ and $R_6$ taken alone are each alkyl having from 1 to 8 carbon atoms, and $R_3$ taken together with $R_4$ and $R_6$ taken together with $R_5$ are alkyl chains each having from 2 to 5 carbon atoms connecting the 5' carbon to the nitrogen attached to the 6' carbon and connecting the 4' carbon to the nitrogen attached to the 3' carbon, respectively. Preferably, $R_3$ and $R_6$ taken alone are alkyl each having from 1 to 3 carbon atoms, and $R_3$ taken together with $R_4$ and $R_6$ taken together with $R_5$ form alkyl chains each having from 2 to 3 carbon atoms connecting the 5' carbon to the nitrogen attached to the 6' carbon and connecting the 4' carbon to the nitrogen attached to the 3' carbon, respectively. Most preferably, $R_3$ and $R_6$ taken alone are methyl or ethyl, and $R_3$ taken together with $R_4$ and $R_6$ taken together with $R_5$ are alkyl chains each having 3 carbon atoms connecting the 5' carbon to the nitrogen attached to the 6' carbon and connecting the 4' carbon to the nitrogen attached to the 3' carbon, respectively.

$R_4$ and $R_5$ taken alone are hydrogen, alkyl having from 1 to 8 carbon atoms, halogen, alkylether having from 1 to 8 carbon atoms, or alkylthioether having from 1 to 8 carbon atoms, and $R_4$ taken together with $R_3$ and $R_5$ taken together with $R_6$ are alkyl chains each having from 2 to 5 carbon atoms as described above. Preferably, $R_4$ and $R_5$ taken alone are hydrogen, chloro, alkyl having from 1 to 3 carbon atoms, or alkylether having from 1 to 3 carbon atoms, and $R_4$ taken together with $R_3$ and $R_5$ taken together with $R_6$ are alkyl chains each having from 2 to 3 carbon atoms as described above. Most preferably, $R_4$ and $R_5$ taken alone are hydrogen, and $R_4$ taken together with $R_3$ and $R_5$ taken together with $R_6$ are alkyl chains each having 3 carbon atoms connecting the 5' carbon to the nitrogen attached to the 6' carbon and connecting the 4' carbon to the nitrogen attached to the 3' carbon, respectively.

L represents a linking functionality whose character depends on the nature of the group to which it is to be attached (referred to herein as a "complementary functionality"). Exemplary linking fuctionalities are listed in Table I together with their complementary functionalities and resulting linking groups. The most preferred linking functionality is a phosphoramidite, which when reacted with a hydroxyl complementary functionality forms a phosphite ester linking group which, in turn, is oxidized to give a phosphate ester linking group.

TABLE I

| Linking Functionality | Complementary Functionality | Linking Group |
|---|---|---|
| —NCS | —NH$_2$ | —NH—CS—NH— |
| (dichlorotriazine) | —NH$_2$ | (monoamino-chlorotriazine) |
| (NHS ester) | —NH$_2$ | —C(O)—N(H)— |
| (maleimide) | —SH | (thioether adduct) |
| —O—P(N(CH(CH$_3$)$_2$)$_2$)(OMe) | HO— | —O—P(O—)(OMe) |

$W_1$, $W_2$, and $W_3$ are hydrogen or chloro, and preferably hydrogen.

As used herein the terms "rhodamine X" (abbreviated "ROX") shall refer to the compounds of Formula I wherein $R_1$ and $R_2$, $R_3$ and $R_4$, $R_5$ and $R_6$, and $R_7$ and $R_8$ are taken together to form 3 carbon alkyl chains as described above, B is carboxylate, and $W_1$, $W_2$, and $W_3$ are hydrogen, and wherein the linking functionality is attached to the 5- or 6- carbons, respectively. As used herein the terms "tetramethylrhodamine" (abbreviated "TMR") shall mean the compounds of Formula I wherein $R_1$, $R_4$, $R_5$ $R_8$, $W_1$, $W_2$, and $W_3$ are hydrogen, B is carboxylate, and $R_2$, $R_3$, $R_6$, and $R_7$ are methyl, and wherein the linking functionality is attached to the 5- or 6- carbons, respectively.

Some rhodamine dyes for use with the invention are available commercially, e.g. Eastman Kodak Company (Rochester, New York), Molecular Probes, Inc. (Junction City, OR), or Research Organics (Cleveland, OH), and others can be synthesized in accordance with the teachings of U.S. Pat. Nos. 2,242,572; 2,153,059; 3,822,270; 3,932,415; and 4,005,092, all of which are incorporated by reference.

ROX and TMR are the most preferred rhodamine dyes for use with the invention.

Detailed descriptions of the procedures for solid phase synthesis by phosphite-triester, phosphotriester, and H-phosphonate chemistries are widely available, e g. Itakura, U.S. Pat. No. 4,401,796; Caruthers et al, U.S. Pat. Nos. 4,458,066 and 4,500,707; Matteucci et al, J Amer. Chem. Soc., Vol. 103, pgs. 3185-3191 (1981); Caruthers et al, Genetic Engineering, Vol. 4, pgs. 1-17 (198 ); Jones, chapter 2, Atkinson et al, chapter 3, and Sproat et al, chapter 4, in Gait, ed., Oligonucleotide Synthesis: A Practical Approach (IRL Press, Washington, D.C., 1984); Froehler et al, Tetrahedron Letters, Vol. 27, Pgs. 469-472 (1986); Garegg et al, Tetrahedron Letters, Vol. 27, pgs. 4051-4054 and 4055-4058 (1986); and Froehler et al, Nucleic Acids Research, Vol. 14, pgs. 5399-5407 (1986) Accordingly, these references are incorporated by reference.

Preferably, the present invention involves synthesis of rhodamine-labeled oligonucleotides by the phosphite triester approach. That is, nucleotides are successively added to a growing chain of nucleotides by reacting nucleoside phosphoramidites with the 5'hydroxyl of the growing chain.

In particular, oligonucleotides are labeled by reacting a rhodamine phosphoramidite with the 5' hydroxyl of the attached oligonucleotide.

Rhodamine phosphoramidites of the invention are made by first reacting the 5- or 6-N-hydroxysuccinimide (NHS) ester of rhodamine with an amino alcohol, e.g. ethanol amine, hexanol amine, or the like, in N,N-dimethylformamide (DMF), or like aprotic polar solvent, at room temperature to form a 5- or 6-alcohol amide of the rhodamine dye, which is then separated from the reaction mixture by standard means. The alcohol amide of the rhodamine dye is then reacted with an excess of di-(N,N-diisopropylamino)methoxyphosphine at room temperature in acetonitrile containing catalytic amounts of tetrazole and diisopropylamine, to form the rhodamine phosphoramidite, which is separated from the reaction mixture.

Generally, cleavage and deprotection are effected by the cleavage reagent of the invention by first exposing an oligonucleotide attached to a solid phase support (via a base-labile bond) to the cleavage reagent at room temperature for about 1-2 hours so that the oligonucleotide is released from the solid support, and then heating the cleavage reagent containing the released oligonucleotide for about 20 to about 60 minutes at about 80° to about 90° so that the protection groups attached to the exocyclic amines are removed. Alternatively, the deprotection step can take place at a lower temperature, but the reaction will take longer to complete, e.g. the heating can be at 55° C. for 5 hours.

After cleavage and deprotection, the labeled or unlabeled oligonucleotides are purified by standard procedures, e.g. Applied Biosystems Users Bulletin No. 13 (Apr. 1, 1987 Revision); or Chapters 5 and 6 in Gait, *Oligonucleotide Synthesis: A Practical Approach* (IRL Press, Washington, D.C., 1984).

EXAMPLES

The following examples serve to illustrate the present invention. The concentrations of reagents, temperatures, and the values of other variable parameters are only to exemplify the invention and are not to be considered limitations thereof.

EXAMPLE I Preparation of Aminoalkylphosphoramidite Linking Agents

Below general procedures for preparing aminoalkylphosphoramidites is disclosed. Roughly, the same procedures are disclosed by Connolly in *Nucleic Acids Research*, Vol. 15, pgs. 3131-3139 (1987). These compounds are useful for amino derivatizing oligonucleotides attached to a solid phase support. One group of aminoalkylphosphoramidites useful in the present invention are defined by the following formula:

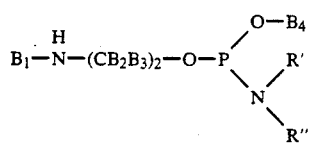

Formula II wherein:

$B_1$ represents an acid-labile or base-labile amino protection group which can be removed without cleaving the base-labile linking group between the solid phase support and the oligonucleotide. Such protection groups are described by Greene, in *Protective Groups in Organic Synthesis* (John Wiley & Sons, New York, 1981), chapter 7, which chapter is incorporated by reference. Preferably base-labile protection groups when taken together with the nitrogen of the heterocycle or that of its precursor, are base-labile amide and carbamate protection groups, preferably trihaloacetyls, acetoacetyl, and fluorenylmethyl carbamates, particularly 9-fluorenylmethyl carbamate and 9-(2-sulfo)-fluorenylmethyl carbamate, and trifluoroacetyl. Preferable acid-labile protection groups include underivatized trityl, and its lower (containing from 1-3 carbon atoms) alkoxy derivatives, particularly 4-monomethoxytrityl. $B_2$ and $B_3$ taken separately each represent hydrogen, lower alkyl, lower substituted alkyl, particularly halo-, cyano-, or nitrosubstituted lower alkyl, lower acyl, cyano, halo, and nitro; more preferably $B_2$ and $B_3$ taken separately each represent hydrogen, lower alkyl, and lower haloalkyl; and most preferably $B_2$ and $B_3$ represent hydrogens.

$B_4$ represents alkyl, alkenyl, aryl, aralkyl, or cyclolkyl containing up to 10 carbon atoms. More preferably, $B_4$ represents lower alkyl; electron-withdrawing beta-substituted ethyl, particularly beta-trihalomethyl-, beta-cyano-, beta-sulfo-, beta-nitrosubstituted ethyl, or the like; electron-withdrawing substituted phenyl, particularly halo-, sulfo-, cyano-,or nitro-, substituted phenyl; or electron-withdrawing substituted phenylethyl. Most preferably, $B_4$ represents methyl, beta-cyanoethyl, or 4-nitrophenylethyl.

The term "lower alkyl" as used herein denotes straight-chain and branched-chain alkyl groups containing from 1-6 carbon atoms, e.g. methyl, ethyl, propyl, isopropyl, tert-butyl, isobutyl, sec-butyl, neopentyl, tert-pentyl, and the like. "Lower substituted alkyl" denotes lower alkyl having electron-withdrawing substituents, such as halo, cyano, nitro, sulfo, or mono-, di-, or trihalomethyl, or the like. "Lower haloalkyl" denotes a lower alkyl with one or more halogen atom substituents, usually fluoro, chloro, bromo, or iodo. "Lower acyl" denotes an acyl containing from 1-7 carbon atoms wherein the non-double bonded carbons comprise a lower alkyl, possibly having halo-, cyano-, or nitro- substituents. "Electron-withdrawing" denotes the tendancy of a substituent to attract valence electrons of the molecule of which it is apart, i.e. it is electroegative, March, *Advanced Organic Chemistry*, Third Ed. (John Wiley, New York, 1985).

j is in the range of 2 to 10.

R' and R'' taken separately each represent alkyl, aralkyl, cycloalkyl, and cycloalkylalkyl containing up to 10 carbon atoms. Preferably R' and R'' taken separately represent lower alkyl, and most preferably when the above phosphoramidites are used directly as linking agents, R' and R'' taken separately are sterically hindering lower alkyls which enhance the chemical stability of the phosphoramidites, and hence their shelf lives. Such sterically hindering lower alkyls include isopropyl, t-butyl, isobutyl, sec-butyl, neopentyl, tert-pentyl, isopentyl, sec-pentyl, and the like.

R' and R'' taken together form an alkylene chain containing up to 5 carbon atoms in the principal chain and a total of up to 10 carbon atoms with both terminal valence bonds of said chain being attached to the nitrogen atom to which R' and R'' are attached; or R' and R'' when taken together with the nitrogen atom to which they are attached form a saturated nitrogen heterocycle which may contain one or more additional heteroatoms from the group consisting of nitrogen, oxygen, and sulfur. More preferably, R' and R'' taken together and with the nitrogen to which they are attached represent pyrrolidino, morpholino, or piperidino. Most preferably, R' and R'' taken together and with the nitrogen to which they are attached represent morpholino.

Another group of aminoalkylphosphoramidites which may be used in the invention include those defined by the following formula:

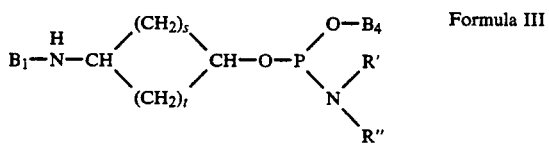

Formula III wherein $B_1$, $B_4$, R', and R'' are as indicated above, and t is in the range of 0 to 8, and s is in the range of 0 to 8. The general procedure for synthesizing the above aminoalkylphosphoramidites Formulas II and III comprises the following steps. Halo-substituted-N,N-di-substituted-O-substituted phosphine, defined by the formula:

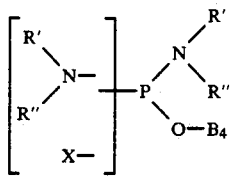

wherein X is a halogen, usually chloro, and R', R", and B₄ are as indicated above, is reacted with an amino-protected alcohol amine defined by the formula:

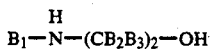

wherein $B_1$, $B_2$, and $B_3$ are as indicated above, in an aprotic solvent, such as dichloromethane, or the like, containing a non-nucleophilic base, for example a trialkylamine, such as N,N-diisopropylethyl amine, or the like, which absorbs the halogen acid released during the reaction. Preferably the reaction takes place under an inert atmosphere, such as argon. Acid conditions in the reaction mixture should be avoided as acid causes the amine of the phosphoramidite product to protonate, and thereby become reactive. The nonnucleophilic base reduces the likelihood of side reactions between the base and activated phosphoramidites.

After reacting the above materials, the reaction mixture, hereinafter referred to as the first reaction mixture, is washed with a mildly basic solution to remove salts of the non-nucleophilic base. Finally, the first reaction mixture is dried, e.g. with $MgSO_4$, $Na_2SO_4$, or the like, to give a protected aminoalkylphosphoramidite.

A. Preparation of a protected aminoethylphosphoramidite.

Chloro-N,N-diisopropylaminomethoxy phosphine (5.0 ml, available form Aldrich Chemical Co., Milwaukee, WI) was added dropwise at 0° C. to a stirred solution of N-2-hydroxyethyl)-2,2,2-trifluoroacetamide (3.9 g) and diisopropylethylamine (5.0 ml) in dichloromethane (about 40 ml) under argon. (N-(2-hydroxyethyl)-2,2,2trifluoroacetamide is synthesized following the procedures disclosed by Lazarus and Benkovic in *J. Am. Chem. Soc.*, Vol. 101, pgs. 4300–4312 (1979): Ethyl trifluoroacetate (56.8g, 0.4 mol) in 50 mL of chloroform is added dropwise to a stirred solution of 24.4 g (0.4 mol) of ethanolamine in 50 mL of chloroform. The solution is stirred at room temperature for 5 h, rotary evaporated to remove the solvent, and distilled at 115° C. (4.3 Torr) to give 58.5 g of oil that crystallized upon scratching.) After stirring at room temperature for 0.5 hours the reaction mixture was washed twice with 0.2 M potassium carbonate solution and once with brine, dried ($MgSO_4$), and concentrated under reduced pressure to give N-(2-(N',N'-diisopropylaminomethoxyphosphinyloxy)ethyl)-2,2, 2trifluoroacetamide as a colorless liquid (7.77 g).

$^1$H-NMR ($CD_2Cl_2$): $\delta$3.6 (6H, m), 3.4 (3H, d, J=12), 1.2 (12H, d, J=6.5)

$^{31}$P-NMR ($CD_2Cl_2$, $^1$H decoupled): $\delta$149(s)

B. Preparation of a protected aminopropylphosphoramidite.

Chloro-N,N-diisopropylaminomethoxy phosphine (3.7 ml) was added dropwise at 0° C. to a stirred solution of N-(3- hydroxypropyl)-2,2,2-trifluoroacetamide (2.9 g, synthesized from 3-amino-1-propanol and ethyl- trifluoroacetate in a manner similar to that disclosed by Lazarus and Benkovic, *J. Amer. Chem. Soc.*, Vol.101, pgs. 4300–4312 (1979)) and diisopropyl-ethylamine (3.7 ml) in dichloromethane (about 20 ml) under argon. After stirring at room temperature for 3 hours, the reaction mixture was poured into hexane (100 ml) and stirred. The mixture was allowed to settle and the supernatant was separated and concentrated under reduced pressure to give N-(3-(N',N'-diisopropylamino-methoxyphosphinyloxy)propyl)-2,2,2-trifluoroacetamide as a colorless liquid (5.2 g).

$^{31}$P-NMR ($CH_2Cl_2$, $^1$H decoupled): $\delta$149 (s)

C. Amino-derivatization of an oligonucleotide by aminoethylphosphoramidite.

After detritylation of the 5' hydroxyl of an oligonucleotide attached to a solid phase support, a 9-fluorenylmethyl-protected aminoethylphosphoramidite is added at a concentration of about 0.2 M in the standard acetonitrile/tetrazole reaction solvent for phosphite triester synthesis. The 9-fluorenylmethyl-protected aminoethylphosphoramidite is prepared the same as the material of part A, except that N-(2-hydroxyethyl)-2,2,2-trifluoroacetamide is replaced by N-(2-hydroxyethyl)-9-fluorenylmethyl carbamate, as also disclosed by Agrawal et al, *Nucleic Acids Research*, Vol 14, pg. 6227 (1986). The 9-fluorenylmethyl protection group is removed at room temperature by an 80:20 percent (by volume) solution of acetonitrile and piperidine. The above reactions are carried out on a standard automated DNA synthesizer, such as an Applied Biosystems model 380A, or like instrument.

EXAMPLE II

Synthesis of ROX-phosphoramidite

A mixture of 97.1 mg (0.158 mmole) of the ethanolamine amides of 5- and 6-carboxy-X-rhodamine and 13.5 mg (0.079 mmole) of diisopropylammonium tetrazolide was purged with dry argon and diluted with 8 mL of dry (distilled from calcium hydride) acetonitrile; 0.40 g (1.53 mmole) of methoxy-bis(diisopropylamino)-phosphine was added and the solution was stirred at room temperature under argon. After two hours, the solution was washed four times with 7 mL portions of hexane, diluted to 200 mL with chloroform containing 0.5% triethylamine, washed with 100 mL of 1:1 brine:-water, dried with sodium sulfate, filtered, and evaporated to dryness. The gummy solid was triturated with hexane and dried under high vacuum; this process was repeated until a dark, free flowing solid was obtained, yielding 113 mg of ROX-5- and ROX-6-phosphoramidites.

EXAMPLE III

Synthesis of TMR-phosphoramidite

A mixture of 61.4 mg (0.130 mmole) of the ethanolamine amides of 5- and 6-carboxyltetramethylrhodamine and 0.26 mL of an acetonitrile solution of 0.005 M diisopropylammonium tetrazolide (0.0013 mmole) were combined and evaporated to dryness at <0.1 mm pressure, and then purged with argon and diluted with 10 mL of dry (distilled from calcium hydride) acetonitrile; 0.22 g (0.840 mmole) of methoxy-bis-(diisopropylamino)phosphine was added and the solution was stirred for 1.5 hours at room temperature under argon. The resulting reaction mixture was washed five times with 5 mL portions of hexane, diluted to 100 mL with chloroform containing 0.5% triethylamine, washed with 60 mL of 1:1 brine:water, dried with sodium sulfate, filtered, and triturated with hexane and evaporated to dryness under high vacuum; this process was repeated until a dark, free flowing solid was obtained, yielding 67.6 mg of TMR-5- and TMR-6-phosphoramidites.

EXAMPLE IV

Cleavage and Deprotection of a protected Oligonucleotide Attached Via a Succinimate Ester to a Solid Phase Support by 1:2:1 Methan: Water:t-Butylamine In this example a protected 18-mer oligonucleotide was synthesized by the phosphite triester method on an Applied Biosystems model 380B DNA synthesizer. The usual cleavage reagent, ammonium hydroxide, was replaced by the cleavage reagent of the invention: methanol:water:t-butylamine in a 1:2:1 ratio, respectively. The synthesizer was reprogrammed so that the solid support and attached oligonucleotide in the reaction vessel were successively exposed to the cleavage reagent four times for 1500 seconds (4×1500) at room temperature. The reaction vessel effluants were collected in a separate vessel and were heated to 85° C. for 40 minutes for deprotection. The reaction mixture was removed and the 18-mer was separated from the reaction mixture by HPLC. After removal, the solid phase support was treated with concentrated ammonium hydroxide in accordance with the standard cleavage protocol of the ABI model 380B. The reaction mixture from the ammonium hydroxide cleavage was then analyzed by HPLC to determine whether additional oligonucleotides were removed from the solid phase support. Comparison of the chromatograms of the two reaction mixtures indicated that 100 percent of the oligonucleotides were removed from the solid phase support by the initial cleavage reaction.

The same oligonucleotide was synthesized again with an identical protocol, except that the duration of the cleavage step with the 1:2:1 methanol:water:t-butylamine cleavage reagent was 4×900 sec instead of 4×1500 sec. HPLC analysis indicated that 71 percent of the oligonucleotides were cleaved in the initial cleavage reaction.

EXAMPLE V

Cleavage and Deprotection of a Protected Oligonucleotide Attached Via a Succinimate Ester to a Solid Phase Support by 1:1:1 Methanol:Water:t-Butylamine The cleavage and deprotection in this example was carried out on the same synthesizer and with the same protocol as in Example IV, except that the cleavage reagent was methanol:water:t-butylamine in a 1:1:1 ratio. HPLC analysis indicated that approximately 80 percent of the oligonucleotides were cleaved from the solid phase support.

EXAMPLE VI

Cleavage and Deprotection of a Protected Oligonucleotide Attached Via a Succinimate Ester to a Solid Phase Support by 2:2:1 Methanol:Water:t-Butylamine The cleavage and deprotection in this example was carried out on the same synthesizer and with the same protocol as in Example IV, except that the cleavage reagent was methanol:water:t-butylamine in a 2:2:1 ratio. HPLC analysis indicated that approximately 10 percent of the oligonucleotides were cleaved from the solid phase support.

EXAMPLE VII

Solid Phase Synthesis of TMR- and ROX-Labeled Oligonucleotide and Cleavage and Deprotection With 1:2:1 Methanol:Water:t-Butylamine ROX and TMR labeled oligonucleotides were separately synthesized on an Applied Biosystems model 380B automated DNA synthesizer. Comparable DNA synthesizers using the phosphite triester chemistry could also be used. Labeling was accomplished by reacting either a ROX phosphoramidite or a TMR phosphoramidite with the 5' hydroxyl of the oligonucleotide attached to the solid phase support under conditions recommended by the manufacturer for attaching nucleoside phosphoramidites. Caruthers et al, U.S. Pat. No. 4,415,732, and Caruthers et al, *Genetic Engineering*, Vol. 4, pgs. 1–17 (1982), provide detailed descriptions of the chemistry used by the Applied Biosystems model 380B synthesizer. Accordingly, these references are incorporated by reference for those descriptions. The ROX and TMR phosphoramidites were used as 0.2 M acetonitrile solutions in combination with a 0.5 M tetrazole/acetonitrile solution to form an activated reagent in the synthesis cycle. Cleavage and deprotection were carried out as described in Example IV. The integrity of the ROX and TMR labeled oligonucleotides were confirmed by comparison with authentic samples using HPLC, polyacrylamide gel electrophoresis, and fluorescent dideoxy DNA sequencing.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. The compound defined by the formula:

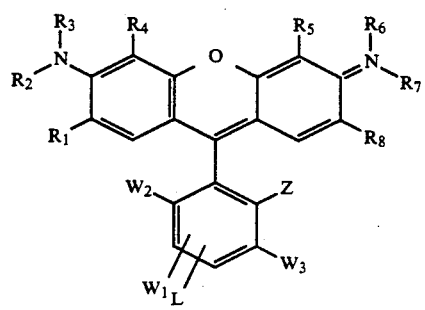

wherein:

L is a phosphoramidite defined by the formula:

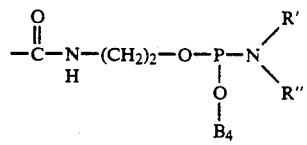

wherein:

j is in the range of 2 to 6;

$B_4$ is alkyl, alkenyl, aryl, aralkyl, or cycloalkyl containing up to 10 carbon atoms;

R' and R" taken separately each represent alkyl, aralkyl, cycloalkyl, and cycloalkylalkyl containing up to 10 carbon atoms; and R' and R" taken together form an alkylene chain containing up to 5 carbon atoms in the principal chain and a total of up to 10 carbon atoms with both terminal valence bonds of said chain being attached to the nitrogen atom to which R' and R" are attached; or R' and R" when taken together with the nitrogen atom to which they are attached from a saturated nitrogen heterocycle which contains one or more heteroatoms from the group consisting of nitrogen, oxygen, and sulfur;

Z is carboxylate or sulfonate;

$R_1$ and $R_8$ taken alone are each hydrogen, halogen, alkyl having from 1 to 8 carbon atoms, alkylether having from 1 to 8 carbon toms, or alkylthloether having from 1 to 8 carbon atoms, and $R_1$ taken together with $R_2$ and $R_8$ taken together with $R_7$ are alkyl chains each having from 2 to 5 carbon atoms connecting the 7' carbon to the nitrogen attached to the 6' carbon and connecting the 2' carbon to the nitrogen attached to the 3' carbon, respectively;

$R_2$ and $R_7$ taken alone are each alkyl having from 1 to 3 carbon atoms;

$R_3$ and $R_6$ taken alone are each alkyl having from 1 to 8 carbon atoms, and $R_3$ taken together with $R_4$ and $R_6$ taken together with $R_5$ are alkyl each having from 2 to 5 carbon atoms connecting the 5' carbon to the nitrogen attached to the 6' carbon and connecting the 4' carbon to the nitrogen attached to the 3' carbon, respectively;

$R_4$ and $R_5$ taken alone are hydrogen, alkyl having from 1 to 8 carbon atoms, alkether having from 1 to 8 carbon atoms, alkthloether having from 1 to 8 carbon atoms, or halogen; and W1, W2, and W3 are each hydrogen or chloro.

2. The compound of claim 1 wherein said rhodamine is tetramethylrhodamine.

3. The compound of claim 1 wherein said rhodamine is rhodamine X.

4. The compound of claim 1 wherein:

Z is carboxylate;

$R_1$ and $R_8$ taken alone are each hydrogen, alkyl having from 1 to 3 carbon atoms, chloro, or alkylether having from 1 to 3 carbon atoms, and $R_1$ taken together with $R_2$ and $R_8$ taken together with $R_7$ each form an alkyl chain having from 2 to 3 carbon atoms connecting the 7' carbon to the nitrogen attached to the 6' carbon and connecting the 2' carbon to the nitrogen attached to 3' carbon, respectively;

$R_2$ and $R_7$ taken alone are each alkyl having from 1 to 3 carbon atoms, and $R_2$ taken together with $R_1$ and $R_7$ taken together with $R_8$ are alkyl chains each having from 2 to 3 carbon atoms connecting the 7' carbon to the nitrogen attached to the 6' carbon and connecting the 2' carbon to the nitrogen attached to 3' carbon, respectively;

$R_3$ and $R_6$ taken alone are alkyl each having from 1 to 3 carbon atoms, and $R_3$ taken together with $R_4$ and $R_6$ taken together with $R_5$ form alkyl chains each having from 2 to 3 carbon atoms connecting the 5' carbon to the nitrogen attached to the 6' carbon and connecting the 4' carbon to the nitrogen attached to the 3' carbon, respectively;

$R_4$ and $R_5$ taken alone are hydrogen.

5. The compound of claim 4 wherein:

$B_4$ is methyl, $\beta$-cyanoethyl, or 4-nitrophenylethyl;

R' and R" taken separately are selected from the group consisting of isopropyl, t-butyl, isobutyl, sec-butyl; and R' and R" taken together is morphollno.

* * * * *

UNITED STATES PATENT AND TRADEMARK OFFICE
CERTIFICATE OF CORRECTION

PATENT NO. : 5,231,191
DATED : July 27, 1993
INVENTOR(S) : Woo, et. al.

It is certified that error appears in the above-indentified patent and that said Letters Patent is hereby corrected as shown below:

Col. 7, lines 33-40: Correct the portion of the formula reading "$(CB_2 B_3)_2$" to read --"$(CB_2 B_3)_j$" --.

Col. 9, lines 15-17: Correct the portion of the formula reading "$(CB_2B_3)$" to read -- $(CB_2B_3)_j$ --

Col. 13 lines 1-8: Correct the portion of the formula reading "$(CH_2)_2$" to read -- $(CH_2)_j$ --

Col. 13, line 30: Delete "toms" and replace it with the word --atoms--.

Col. 13, line 30: Delete "alkylthloether" and replace it with the word -- "alkylthioether--

Col. 14, line 43: Delete "morphollino" and replace it with the word -- morpholino--

Signed and Sealed this

Fifth Day of April, 1994

Attest:

Attesting Officer

BRUCE LEHMAN

Commissioner of Patents and Trademarks